(12) United States Patent
Jones

(10) Patent No.: US 6,973,678 B2
(45) Date of Patent: Dec. 13, 2005

(54) EASILY ASSEMBLED SPECIMEN CONTAINER

(76) Inventor: Timothy B. Jones, 1405 Boomer Trail, Edmond, OK (US) 73034

( * ) Notice: Subject to any disclaimer, the term of this patent is extended or adjusted under 35 U.S.C. 154(b) by 0 days.

(21) Appl. No.: 10/098,102

(22) Filed: Mar. 13, 2002

(65) Prior Publication Data

US 2003/0172446 A1 Sep. 18, 2003

(51) Int. Cl.$^7$ .............................. A47K 11/12; B01L 3/00
(52) U.S. Cl. ........................ 4/144.1; 402/122; 600/573
(58) Field of Search .............................. 4/144.1–144.3; 402/102; 600/573

(56) References Cited

U.S. PATENT DOCUMENTS

| | | | |
|---|---|---|---|
| 3,518,164 A | 6/1970 | Andelin et al. | |
| 3,777,739 A | 12/1973 | Raitto | |
| 3,881,465 A | 5/1975 | Raitto | |
| 4,137,573 A | * 2/1979 | Kroeger | 4/144.1 |
| 4,176,412 A | 12/1979 | Peterson | |
| 4,244,920 A | 1/1981 | Manschot et al. | |
| 5,174,985 A | 12/1992 | Schwarz et al. | |
| D335,176 S | 4/1993 | Jones et al. | |
| D335,177 S | 4/1993 | Jones et al. | |
| D335,178 S | 4/1993 | Jones et al. | |
| D335,179 S | 4/1993 | Jones et al. | |
| D335,180 S | 4/1993 | Jones et al. | |
| 5,202,094 A | 4/1993 | Jones et al. | |
| D335,346 S | 5/1993 | Jones et al. | |
| D335,708 S | 5/1993 | Jones et al. | |
| D338,064 S | 8/1993 | Jones et al. | |
| D341,883 S | 11/1993 | Jones et al. | |
| D353,669 S | 12/1994 | Jones et al. | |
| D357,066 S | 4/1995 | Jones et al. | |
| 5,445,292 A | 8/1995 | Slomski et al. | |
| D364,458 S | 11/1995 | Jones et al. | |
| 5,558,840 A | 9/1996 | Jones et al. | |
| D379,655 S | 6/1997 | Savignac | |
| D398,993 S | 9/1998 | Jones | |
| D399,007 S | 9/1998 | Jones et al. | |
| D408,913 S | 4/1999 | Jones | |
| 6,572,827 B2 * | 6/2003 | Wilkinson et al. | 422/102 |

* cited by examiner

Primary Examiner—Charles E. Phillips

(57) ABSTRACT

A device for collecting biological specimens having a container and a detachable handle. The handle allows a person to position the container so that contact between the person and sample is minimized or avoided. The handle includes a hoop into which the container slides from the container's lower end. The container is configured with projections on its outer surface that frictionally engage the hoop. Alternatively, the container can be configured with projections, a ring, or a lip over which the hoop is obliquely traversed to prevent the hoop from sliding downward on the outer surface of the container. The handle is constructed of a flexible material so that it may deform as needed when engaging the outer surface of the container.

18 Claims, 3 Drawing Sheets

EASILY ASSEMBLED SPECIMEN CONTAINER

BACKGROUND OF THE INVENTION

1. Field of the Invention

The invention relates generally to specimen gathering devices in the medical field to collect biological samples from patients, and in particular to an improved specimen container and handle.

2. Description of the Related Art

Patients are often required to provide samples of urine or stool so that their treating physician can properly diagnose an illness. Also, employees are often required to produce urine samples for drug testing. Although in many situations the patient or employee is allowed to produce the sample in private, the main drawback is that they or a family member must hold the specimen container while the sample is obtained. Subsequently, the hand of the person holding the container often is soiled while obtaining the specimen.

Other specimen gathering devices as well as handles for holding conventional specimen cups have been proposed so that the hand of the person holding the container is farther away from the container. While reducing the problem of hand soiling, these devices have other problems. Some of the previous proposals are so complicated that they are not easy to assemble, while others are too difficult for the elderly to assemble on their own. Other devices appear to be too expensive to manufacture in mass quantities for disposal after a single use or the devices are bulky and difficult to package.

SUMMARY OF THE INVENTION

A device for collecting a specimen from a patient has a container for holding the specimen as it is deposited and a handle having a hoop for holding the container. The container has a downward facing shoulder for engagement by the hoop, the handle being located near the upper portion of the container. The container rests inside of the hoop with the shoulder in contact with the upper edge of the hoop to prevent the container from sliding through the hoop. The hoop is retained in position on the container by at least one protrusion located around the circumference of the container below the shoulder.

The protrusions are large enough so that the circumference around the radially outermost portions of the protrusions has an effective diameter that is larger than the inner diameter of the hoop of the handle. The protrusions force the hoop to deform as it passes over the protrusions to engage the shoulder. The protrusions can be a series of intermittently spaced objects around the circumference of the container, or a continuous ring that surrounds the container. The protrusions can be adapted so that the lower portion of the protrusion is smaller in diameter to allow the hoop to slide over the protrusions more easily.

The protrusions can be located so that they are in contact with the inner surface of the hoop when the hoop engages with the shoulder. In this location, the protrusions form an interference fit with the inside of the hoop and frictionally keep the hoop from sliding down the container. The protrusions can also be located so that they are below the hoop when the hoop engages the shoulder. In this arrangement, the protrusions are a physical barrier to downward movement of the hoop relative to the container.

The handle and all of the containers are easily mass manufactured so the cost associated with each specimen collector is low. The handles are easily attached to the containers so they are capable of being used by children and the elderly. The handles provide a distance between the cup and the hand to prevent soiling the hand of the person holding the specimen collector while the specimen is deposited.

DETAILED DESCRIPTION OF THE PREFERRED EMBODIMENTS

Figure 1:
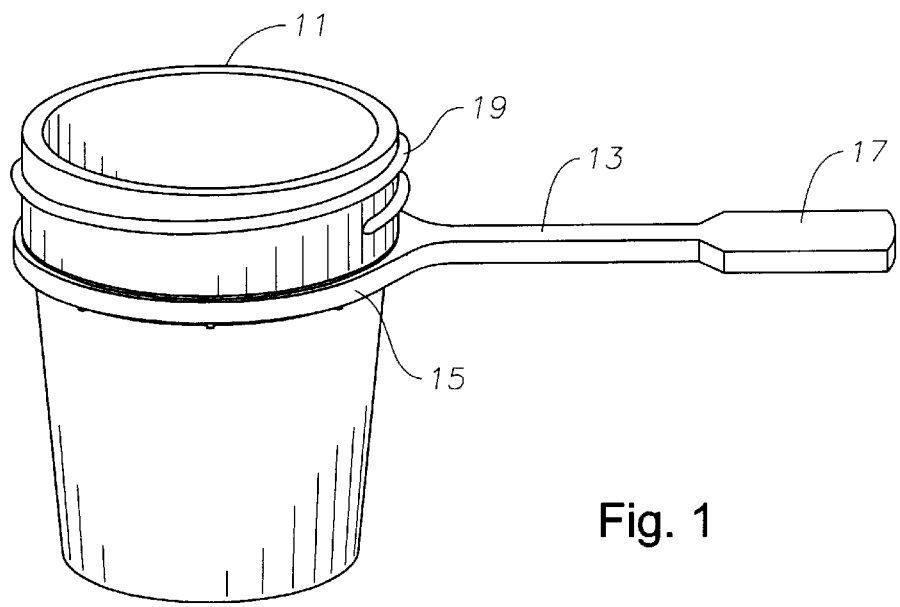
FIG. 1 is a perspective view of a container and handle of a specimen collecting device constructed in accordance with this invention.

Referring to FIG. 1, a container 11 is shown with a handle 13 attached to container 11. Container 11 is a collection cup for specimen samples. Container 11 is for collecting urine, stool, or other specimens for the diagnosis of a patient by a treating physician and for collecting urine for drug testing. In the preferred embodiment, container 11 is formed of a suitable plastic such as polypropylene. Container 11 is substantially cylindrical, having inclined sides making the lower portion of container 11 smaller in diameter than the upper portion. Container 11 has a bottom side enclosing the lower portion of container 11. The top side of container 11 is open for receiving a specimen.

Handle 13 is an elongated member with an integrally formed hoop 15 on one end to slide over the outer surface of container 11 from the lower portion towards the upper portion of container 11. A gripping region 17 is located on the end of handle 13 opposite hoop 15. Handle 13 is a plastic material strong enough for a person holding gripping region 17 to support container 11 after the specimen is deposited in container 11. Preferably, handle 13 is formed of polystyrene although other materials are suitable. Handle 13 is fairly rigid. Hoop 15 may be deformed, but does not readily stretch in diameter in the preferred embodiment so as to provide adequate stability.

Figure 2:
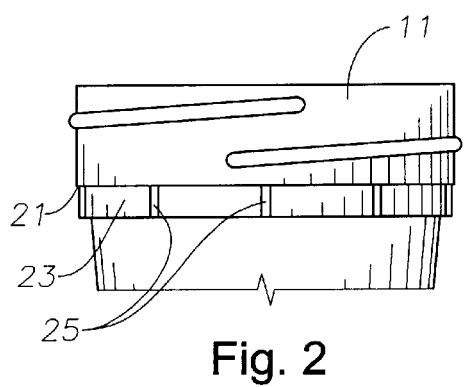
FIG. 2 is an elevational view of one embodiment of a portion of the container shown in FIG. 1.

Threads 19 are located on the outer surface of the upper portion of container 11 for receiving a conventional lid (not shown) having internal threads. Container 11 is closed and sealed to prevent loss of the specimen when threads 19 receive the lid (not shown). Referring to FIG. 2, a downward facing annular shoulder 21 is located on the outer surface of the upper portion of container 11 for receiving the top surface of hoop 15 (shown in FIG. 1). Shoulder 21 is below threads 19. The outer diameter of shoulder 21 is larger than the inner diameter of hoop 15 (FIG. 1), and the top surface of hoop 15 engages shoulder 21. Shoulder 21 is a physical barrier to hoop 15 (FIG. 1) sliding up the outer surface of container 11 to the threads 19. Shoulder 21 prevents container 11 from sliding through hoop 15 when someone holding gripping region 17 supports container 11. An annular engagement zone 23 is defined by the portion of container 11 below shoulder 21. Engagement zone 23 is surrounded by hoop 15 (FIG. 1) when hoop 15 engages shoulder 21. Engagement zone 23 has a vertical dimension or thickness that is slightly more than the thickness of hoop 15 (FIG. 1). In this embodiment, the outer diameter of engagement zone 23 is slightly less than the inner diameter of hoop 15 (FIG. 1).

Referring to FIG. 2, a set of ribs 25 are located in engagement zone 23 around the circumference of container 11 below shoulder 21. Ribs 25 are preferably evenly spaced around the circumference of engagement zone 23. Also, preferably the circumferential space between each rib 25 and another rib 25 is much greater than the circumferential thickness of each rib 25. The outer surface of each rib 25 is a small segment of a cylinder that defines an effective diameter. Ribs 25 are oriented axially along the axis of container 11 so that ribs 25 extend from shoulder 21 towards the lower portion of container 11, preferably terminating at the lower edge of engagement zone 23.

The outer diameter extending around the circumference of the portion of container 11 at the exterior surface of ribs 25 defines an effective diameter that is less than the outer diameter of shoulder 21 and slightly greater than the inner diameter of hoop 15 (FIG. 1). In the preferred embodiment, the effective diameter of ribs 25 is substantially the same around the upper and lower portions of ribs 25. The material of hoop 15 (FIG. 1) is flexible enough for hoop 15 to deform as hoop 15 is pulled upward over ribs 25. Once installed, the inner surface of hoop 15 (FIG. 1) is in contact with the outer surface of ribs 25 when hoop 15 engages shoulder 21. Ribs 25 form an interference fit with the inner surface of hoop 15 (FIG. 1) when hoop engages shoulder 21, the frictional engagement preventing container 11 from rotating inside of hoop 15. Although hoop 15 does not readily stretch when installed, it does tend to flatten between ribs 25 so as to be able to locate over the larger effective diameter of ribs 25.

In operation a patient or operator orients handle 13 (FIG. 1) relative to container 11 so hoop 15 (FIG. 1) is surrounding the lower portion of container 11. The patient moves handle 13 and slides hoop 15 along the inclined sides of container 11 towards the upper portion of container 11. The patient slides hoop 15 (FIG. 1) substantially perpendicular to the long axis of container 11 over ribs 25 until the upper edge of hoop 15 (FIG. 1) engages shoulder 21.

After the patient deposits the specimen in container 11, the patient or a medical technician can disassemble the specimen collecting device. Preferably a lid (not shown) is first installed. To disassemble the device, the patient tilts handle 13 (FIG. 1) to cause hoop 15 (FIG. 1) to disengage from ribs 25 and shoulder 21. The patient or technician then slides hoop 15 down the inclined sides of container 11 until hoop 15 clears the lower portion and no longer surrounds container 11.

Figure 3:
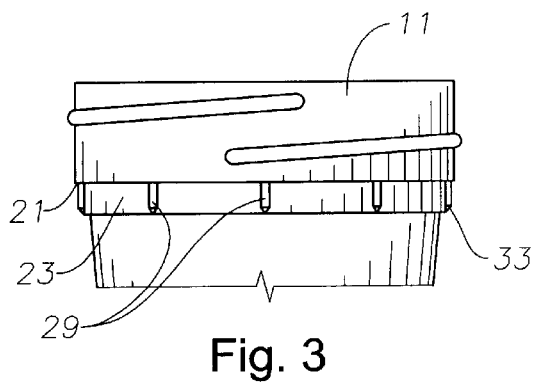
FIG. 3 is an elevational view of another embodiment of a portion of the container shown in FIG. 1.

Referring to FIG. 3, a second embodiment of container 11 is shown having a set of axially oriented tapered ribs 29 in engagement zone 23. Like ribs 25, ribs 29 are spaced around the circumference of container 11. Ribs 29 also have an effective diameter defined around the circumference of the radially outermost portions of ribs 29 that is less than the outer diameter of shoulder 21 and greater than the inner diameter of hoop 15 (FIG. 1).

In the embodiment shown in FIG. 3, ribs 29 have lower portions with inclined faces 33 angling inward from an axially middle portion of ribs 29 to the axially lowermost portion of ribs 29. The effective diameter around inclined faces 33 of ribs 29 is substantially the same or slightly less than the inner diameter of hoop 15 (FIG. 1). The effective diameter around the portion of ribs 29 above inclined faces 33 is larger than the inner diameter of hoop 15 (FIG. 1). The effective diameter around inclined faces 33 allows hoop 15 (FIG. 1) to more slide over the lowermost portions of ribs 29 more easily than in the first embodiment.

Like the first embodiment, hoop 15 (FIG. 1) deforms as hoop 15 engages the portion of ribs 29 above inclined faces 33 because effective diameter is larger than the inner diameter of hoop 15. The inner surface of hoop 15 (FIG. 1) is in frictional contact with the outer surface of the portion of ribs 29 above inclined faces 33 when hoop 15 engages shoulder 21. Ribs 29 form an interference fit with the inner surface of hoop 15 (FIG. 1) when hoop 15 engages shoulder 21, preventing container 11 from sliding too easily from hoop 15. Once installed, the lower edge of hoop 15 (FIG. 1) is above inclined faces 33.

In operation, the patient attaches handle 13 (FIG. 1) relative to container 11 so hoop 15 (FIG. 1) is surrounding the lower portion of container 11. The patient moves handle 13 (FIG. 1) and slides hoop 15 (FIG. 1) along the inclined sides of container 11 towards the upper portion of container 11. The patient slides hoop 15 (FIG. 1) substantially perpendicular to the long axis of container 11, first over inclined faces 33 then over ribs 29 until the lower edge of hoop 15 (FIG. 1) is above inclined faces 33. Inclined faces 33 allow the inner surface of hoop 15 (FIG. 1) to slide over the lower portions of ribs 29 more easily than the inner surface can slide over the lower portions of ribs 25 in the embodiment shown in FIG. 2.

Figure 4:
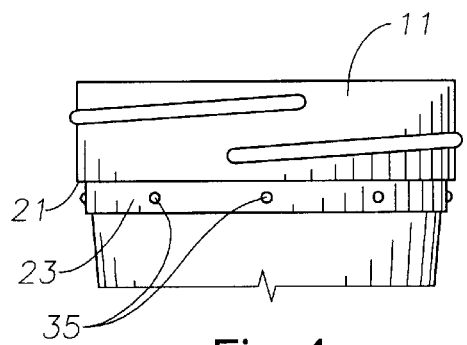
FIG. 4 is an elevational view of another embodiment of a portion of the container shown in FIG. 1.

In the embodiment shown in FIG. 4, a set of protuberances or bosses 35 are located around the outer surface of container 11 in engagement zone 23 below shoulder 21. Bosses 35 are substantially hemispherical in shape and define an effective diameter around the radially outermost portions of bosses 35. Bosses 35 are evenly spaced apart from each other. The spaces between bosses 35 are much greater than the diameter of each bosses 35. The effective diameter around the radially outermost portions of bosses 35 is larger than the inner diameter of hoop 15 (FIG. 1) causing hoop 15 to deform as hoop 15 engages bosses 35. The inner surface of hoop 15 (FIG. 1) is in contact with the radially outermost surface of bosses 35 when hoop 15 engages shoulder 21. Bosses 35 form an interference fit with the inner surface of hoop 15 (FIG. 1) when hoop engages shoulder 21, preventing container 11 from sliding out of hoop 15.

In operation, the patient attaches handle 13 to container 11 in the same manner as the embodiment shown in FIG. 3. The lower portions of hemispherically shaped bosses 35 allow the inner surface of hoop 15 (FIG. 1) to slide over the lower portions of bosses 35 more easily than the inner surface of hoop 15 can slide over the lower portions of ribs 25 in the embodiment shown in FIG. 2. Instead of single bosses 35, two or more bosses could be located at each location, one above the other and perpendicular to the long axis of container 11.

Figure 5:
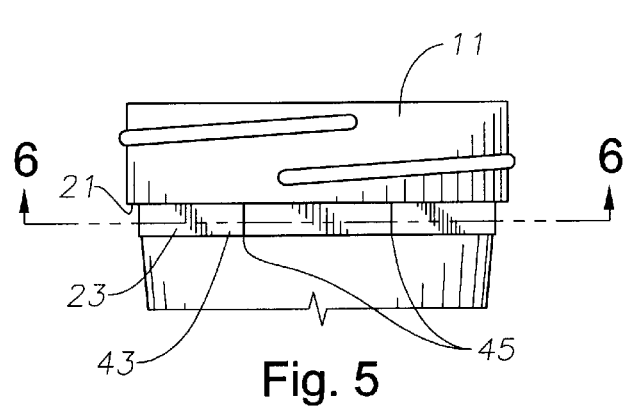
FIG. 5 is an elevational view of another embodiment of a portion of the container shown in FIG. 1.
Figure 6:
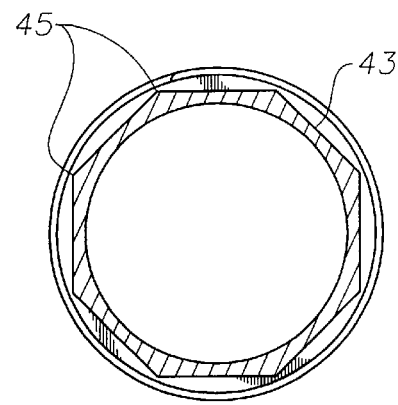
FIG. 6 is a cross-sectional view of the container shown in FIG. 5, taken along the line 6—6 of FIG. 5.

In the embodiment shown in FIGS. 5 and 6, engagement zone 23 comprises a polygonal engagement zone 43 that extends around the outer surface of container 11 below shoulder 21. As shown in FIG. 6, the cross-section of engagement zone 43 is substantially an octagon in shape. A series of points or corners 45 are defined by the intersections of each side of polygonally shaped engagement zone 43. The effective diameter is defined for the circumference extending around points 45 of engagement zone 43. The effective diameter is larger than the diameter of container 11 below engagement zone 43 and smaller than the diameter of shoulder 21. Engagement zone 43 can be other polygonal shapes such as hexagons, heptagons, nonagons, decagons, or the like so long as the effective diameter remains larger than the diameter of the portion of container 11 below engagement zone 43, and smaller than the diameter of shoulder 21.

The effective diameter around points 45 is larger than the inner diameter of hoop 15 (FIG. 1). Hoop 15 deforms as hoop 15 engages polygonal engagement zone 43. The inner surface of hoop 15 (FIG. 1) is in frictional contact with points 45 when hoop 15 engages shoulder 21. Points 45 of polygonal engagement zone 43 form an interference fit with the inner surface of hoop 15 (FIG. 1), preventing container 11 from slipping. In operation, the patient attaches handle 13 to container 11 for this embodiment in the same manner as described for the embodiment in FIG. 2.

Figure 7:
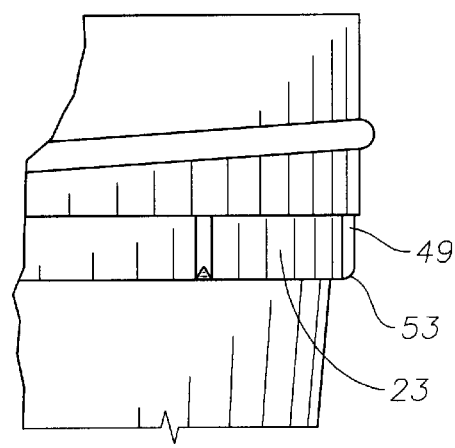
FIG. 7 is an elevational view of another embodiment of a portion of the container shown in FIG. 1.

Referring to FIG. 7, another embodiment is shown having a set of ribs 49 located in engagement zone 23. Ribs 49 are similar to ribs 25 (FIG. 2) but are semi-cylindrical. Ribs 49 are evenly spaced apart and define an effective diameter of the circumference around the outermost portions of ribs 49.

A rounded surface 53 is preferably located on the axially lowermost portion of ribs 49. Rounded surfaces 53 have an effective diameter less than the effective diameter for the upper portion of ribs 49. The effective diameter of rounded surfaces 53 is substantially the same or less than the inner diameter of hoop 15 (FIG. 1). In operation, the patient attaches handle 13 (FIG. 1) to container 11 in the same manner as described for the embodiment in FIG. 3. Rounded surfaces 53 allow the inner surface of hoop 15 (FIG. 1) to slide over ribs 49 more easily. Once installed, the lower side of hoop 15 (FIG. 1) will be above rounded surfaces 53.

Figure 8:
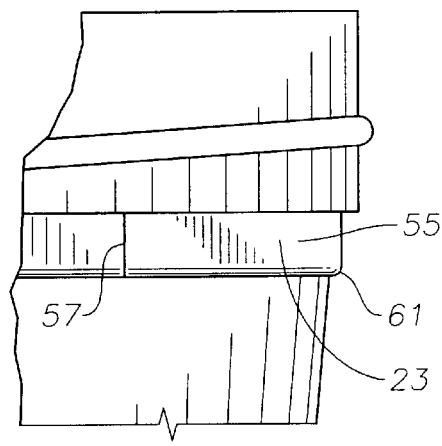
FIG. 8 is an elevational view of another embodiment of a portion of the container shown in FIG. 1.

Referring to FIG. 8, a polygonal engagement zone 55 is located in engagement zone 23. Polygonal engagement zone 55 is similar to engagement zone 43 (FIG. 6), having a set of points 57 at the interfaces of each of the sides of polygonal engagement zone 55. Points 57 define an effective diameter of the circumference around points 57. Engagement zone 55 differs from engagement zone 43 in that the lower portion has a rounded surface 61.

Rounded surface 61 has an effective diameter less than the effective diameter for the upper portion of points 57. Rounded surface 61 has effective diameter substantially the same or less than the inner diameter of hoop 15 (FIG. 1) thereby allowing hoop 15 (FIG. 1) to slide over the lower portion of points 57 more easily. In operation, the patient attaches handle 13 (FIG. 1) to container 11 for this embodiment in the same manner as described for the embodiment of FIG. 3. Once installed, the lower surface of hoop 15 (FIG. 1) is above rounded surface 61.

Figure 9:
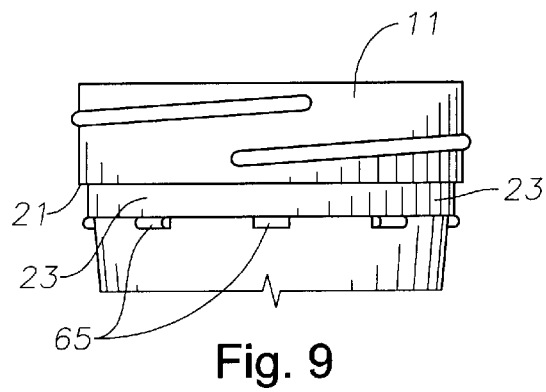
FIG. 9 is an elevational view of another embodiment of a portion of the container shown in FIG. 1.
Figure 10:
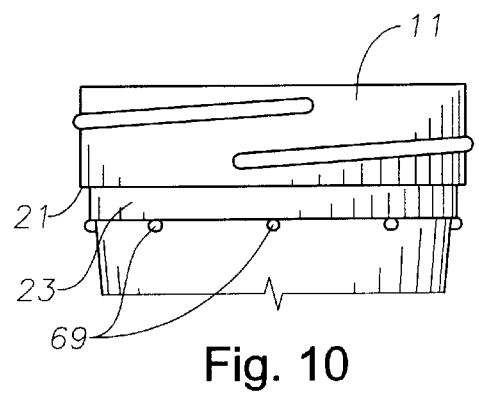
FIG. 10 is an elevational view of another embodiment of a portion of the container shown in FIG. 1.
Figure 11:
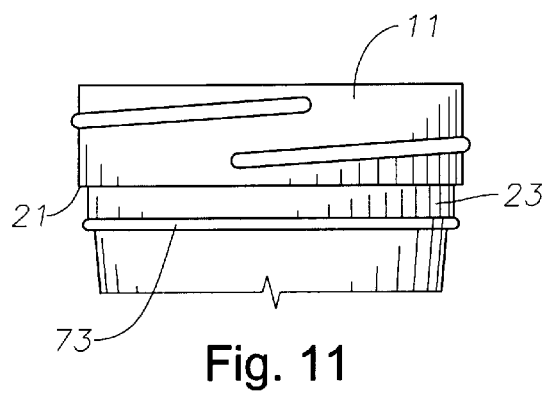
FIG. 11 is an elevational view of another embodiment of a portion of the container shown in FIG. 1.

Referring to FIGS. 9–11, different shaped protrusions are spaced around the circumference of container 11 below engagement zone 23. In the embodiment shown in FIG. 9, the protrusions are substantially half-cylinders 65 evenly spaced around the circumference of container 11 at the lower edge of engagement zone 23. The long axes of half-cylinders 65 are substantially parallel to engagement zone 23 and shoulder 21. Half-cylinders 65 define an effective diameter around the outermost portions of half-cylinders 65 that is greater than the inner diameter of hoop 15 (FIG. 1).

In the embodiment shown in FIG. 10, a series of protruding hemispherical bosses 69 are evenly spaced around the circumference of container 11 at the lower edge of engagement zone 23. Bosses 69 define an effective diameter around the outermost portions of bosses 69 that is greater than the inner diameter of hoop 15 (FIG. 1).

In the embodiment shown in FIG. 11, a barrier ring 73 extends continuously around the circumference of container 11 at the lower edge of engagement zone 23. The outer diameter of ring 73 is greater than the inner diameter of hoop 15 (FIG. 1).

The effective diameters for protrusions 65, 69, and 73 are larger than the outer diameter of engagement zone 23 and the inner diameter of hoop 15 (FIG. 1) for their respective embodiments. In the embodiments shown in FIGS. 9–11, a portion of hoop 15 (FIG. 1) slides over half-cylinders 65, bosses 69, or ring 73, then handle 13 (FIG. 1) is rotated upward. Hoop 15 (FIG. 1) deforms as it slides over protrusions 65, 69, and 73. Once installed hoop 15 (FIG. 1) is located over engagement zone 23 below shoulder 21 and above protrusions 65, 69, or 73. The inner diameter of hoop 15 (FIG. 1) is greater than the outer diameter of engagement zone 23.

Figure 12:
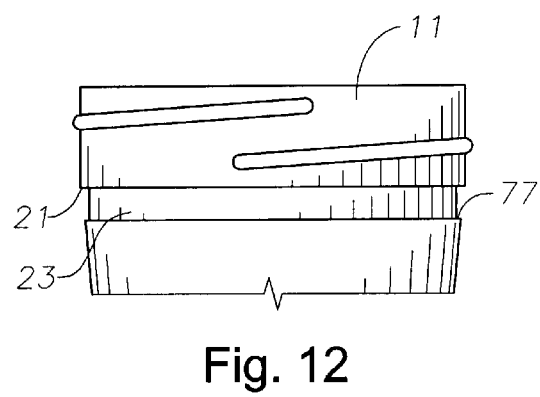
FIG. 12 is an elevational view of another embodiment of a portion of the container shown in FIG. 1.

Referring to FIG. 12, the sidewall portion of container 11 at the lower edge of engagement zone 23 forms a physical barrier to downward movement of hoop 15 (FIG. 1). The outer diameter of the sidewall portion and engagement zone 23 define a lip 77 at the lower edge of engagement zone 23. The diameter of lip 77 is larger than the diameter of engagement zone 23 and larger than the inner diameter of hoop 15 (FIG. 1). Lip 77, like protrusions 65, 69, and 73 (FIG. 9–11), prevents hoop 15 (FIG. 1) from sliding downward relative to container 11.

Figure 13:
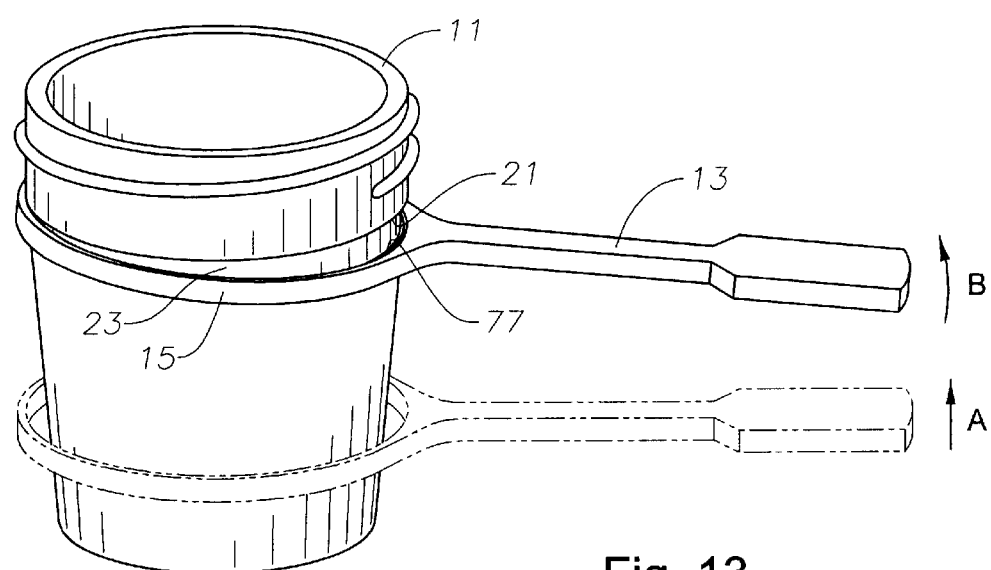
FIG. 13 is an perspective view of the assembly of the specimen collector shown in FIG. 12, and showing the handle being installed.

Referring to FIG. 13, to install hoop 15, the patient moves handle 13 along the exterior surface of container 11 as shown by movement A. The patient then places a portion of hoop 15 above lip 77 with handle 13 inclined as shown in FIG. 13. The user then rotates handle 13 upward as represented with movement B of FIG. 13. Hoop 15 is removed from engagement zone 23 by rotating handle 13 in the opposite direction of movement B. Lip 77 holds hoop 15 in engagement with shoulder 21, which makes collection of specimen an easier task for the patient.

The containers and handles in the embodiments described above are easy to manufacture in mass quantities. The handles do not need to vary depending upon the different embodiments that are chosen. The handle is easily positioned and removed from all of the different embodiments of the containers described above, which allows children or the elderly to assemble the collection device by themselves and in privacy. Thus container and cup reduce the chances for soiling one's hands.

Further, it will also be apparent to those skilled in the art that modifications, changes and substitutions may be made to the invention in the foregoing disclosure. Accordingly, it is appropriate that the appended claims be construed broadly and in the manner consisting with the spirit and scope of the invention herein.

What is claimed is:

1. A specimen collecting device comprising:
   a substantially cylindrical container for receiving a specimen, a top end of the container being open;
   a downward facing shoulder located on an outer surface of an upper portion of the container;
   an annular engagement zone extending downward from the shoulder;
   a detachable handle for holding the container while the specimen is collected;
   a hoop on the end of the handle that that slides over a lower end of the container, extends around the circumference of the outer surface of the container, wherein a top side of the hoop engages the shoulder; and wherein
      a retaining portion on the outer surface of the container below the shoulder has an effective outer diameter greater than an inner diameter of the hoop to selectively retain the hoop on of the engagement zone.

2. The specimen collecting device of claim 1, wherein the retaining portion comprises at least one protrusion that frictionally engages an inner diameter of the hoop when fully installed.

3. The specimen collecting device of claim 1, wherein the retaining portion comprises a series of axially oriented ribs spaced around the outer surface of the container that form a frictional fit with the inner diameter of the hoop when fully installed.

4. The specimen collecting device of claim 3, wherein lower portions of the ribs taper to a smaller effective outer diameter.

5. The specimen collecting device of claim 3, wherein the ribs are substantially half-cylinders.

6. The specimen collecting device of claim 4, wherein the ribs are substantially half-cylinders.

7. The specimen collecting device of claim 1, wherein the retaining portion comprises a series of hemispherical protrusions spaced around the outer surface of the container that form a frictional fit with the inner diameter of the hoop when fully installed.

8. The specimen collecting device of claim 1, wherein the retaining portion comprises a ring extending around entire circumference of the container at a lower side of the engagement zone, the ring being below the hoop when fully installed.

9. The specimen collecting device of claim 1, wherein the engagement zone is a polygonal surface and the retaining portion comprises corner points of the polygonal surface, the points of the polygonal surface forming a frictional fit with the inner diameter of the hoop when fully installed.

10. The specimen collecting device of claim 1, wherein the retaining portion is located at the lower edge of the engagement zone, and has an effective outer diameter greater than the outer diameter of the engagement zone;
   and wherein the hoop fits around the engagement zone above the retaining portion.

11. The specimen collecting device of claim 1, wherein the retaining portion comprises a series of elongated protrusions with axes perpendicular to a longitudinal axis of the container, spaced around the circumference of the container below the engagement zone, the hoop locating between the shoulder and the elongated protrusions.

12. The specimen collecting device of claim 1, wherein the retaining portion comprises a series of substantially hemispherical protrusions spaced around the circumference of the container below the shoulder and separated from the shoulder by an engagement zone of lesser outer diameter than the inner diameter of the hoop, the hoop locating between the shoulder and the substantially hemispherical protrusions.

13. The specimen collecting device of claim 1, wherein the retaining portion comprises a ring located below the shoulder and separated from the shoulder by an engagement zone of lesser outer diameter than the inner diameter of the hoop, the hoop locating between the shoulder and the ring.

14. The specimen collecting device of claim 1, wherein the retaining portion comprises an annular lip located below the shoulder and separated from the shoulder by an engagement zone of lesser outer diameter than the inner diameter of the hoop, the hoop locating between the shoulder and the lip.

15. A specimen collecting device comprising:
   a substantially cylindrical container for receiving a specimen, the top end of the container being open;
   a set of threads adjacent the top end of container;
   a hoop on the end of a detachable handle that that slides over a lower end of the container, and extends around the circumference of the outer surface of the container;
   a downward facing shoulder located on an outer surface of an upper portion of the container below the threads, the shoulder having an outer diameter greater than an inner diameter of the hoop, a top side of the hoop engaging the shoulder when fully installed;
   an annular engagement zone on the outer surface of the container below the shoulder for receiving the hoop; and
   the engagement zone having at least one protrusion located thereon that defines an effective diameter larger than the inner diameter of the hoop, the inner diameter of the hoop being in frictional engagement with the protrusion while fully installed.

16. The specimen collecting device of claim 15, wherein the at least one protrusion comprises a plurality of protrusions spaced around the circumference of the engagement zone.

17. The specimen collecting device of claim 15, wherein the engagement zone comprises a polygonal surface, and the at least one protrusion comprises corner points of the polygonal surface.

18. The specimen collecting device of claim 15, wherein the lower portion of the protrusion is tapered.

* * * * *